United States Patent [19]

Harsy

[11] Patent Number: 4,990,666
[45] Date of Patent: Feb. 5, 1991

[54] RACEMIZATION OF OPTICALLY ACTIVE AMINO ALCOHOLS

[75] Inventor: Stephen G. Harsy, Mt. Airy, Md.

[73] Assignee: W. R. Grace & Co.-Conn, New York, N.Y.

[21] Appl. No.: 18,255

[22] Filed: Feb. 4, 1987

[51] Int. Cl.$^5$ .................. C07C 209/00; C07C 209/88
[52] U.S. Cl. .................................. 564/302; 564/303; 564/304
[58] Field of Search .................. 564/302, 303, 304

[56] References Cited

U.S. PATENT DOCUMENTS 4,096,186  1/1978  Ichikawa et al. .................. 564/302

FOREIGN PATENT DOCUMENTS 2903589  8/1980  Fed. Rep. of Germany ...... 564/302
 671451  5/1952  United Kingdom ................ 564/302

OTHER PUBLICATIONS

Japanese Unexamined Application-Sho 51/6911, Chemical Abstracts, vol. 95, Item 61377m.

*Primary Examiner*—Richard L. Raymond
*Attorney, Agent, or Firm*—Howard J. Troffkin

[57] ABSTRACT

A process for racemization of optically active amino alcohols by subjecting the amino alcohol to hydrogen under moderate temperature and pressure conditions while in contact with Raney cobalt.

28 Claims, No Drawings

RACEMIZATION OF OPTICALLY ACTIVE AMINO ALCOHOLS

BACKGROUND OF THE INVENTION

The present invention is directed to a method of racemizing optically-active amino alcohols to convert the less desired enantiomer to the racemic mixture in high yields.

Various amino alcohols which have a pair of optically active enantiomers are known in which one of the pair has little or no utility while the other has utility in its own right or is useful as a precursor for the synthesis of pharmaceutical agents and the like. For example, of the optically active pair of 2-amino-1-butanol, the levorotatory compound has no utility while the dextrorotatory compound is a starting material for the medicament, Ethambutol.

It is highly desired to have a simple process to convert the less valuable material into the more valuable material. Previous attempts have required anhydrous conditions, the use of hard to handle reagents, the formation of by-products which reduced the yield and hindered separation and recovery of the desired enantiomer and/or provide for low degree of racemization. For example, in an article entitled "A Study on the Racemization of Optically Active-Amino Alcohols" by Seong-Ho Kang, published in Hanguk Saenghiral Kwahak Yonguwan Nouchoung, Vol. 25, p. 9–14 (1980) one is taught that the optical rotation of 2-amino-1-butanol can be changed by treating it with a hydrogenation catalyst in the presence of hydrogen and ammonia. The reference teaches that crystalline by-products form when nickel or cobalt catalysts are used while the by-products are reduced when a specific cobalt-iron oxide which is high in iron content is employed. Japanese Patent Application Sho 51/6911 describes the same conversion but indicates that the best results are obtained by using a reductive cobalt or Urishibara cobalt as the catalyst. These catalysts are formed for example, by depositing a cobalt salt on a substrate and reducing the salt to cobalt metal by treatment with a reducing agent such as zinc, hydrogen or carbon monoxide to produce a supported cobalt catalyst. Both references' methods require the use of ammonia which is both difficult to handle and to dispose of and, therefore, adds to the processing costs.

It is highly desired to provide a process which causes a high degree of racemization, low by-product formation and avoids the need for difficult to handle reagents such as ammonia.

SUMMARY OF THE INVENTION

The present process provides a means to racemize an optically active mixture of amino alcohols by contacting the amino alcohol with Raney cobalt under hydrogen pressure of from 10 to 50 atmospheres and at a temperature of of from 100° C. to 175° C.

DETAILED DESCRIPTION OF THE INVENTION

The present invention provides a process of racemizing an optically-active mixture of alpha-amino alcohols having the general formula

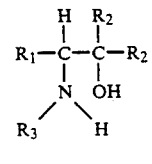

or

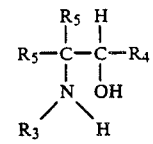

wherein $R_1$ represents an alkyl group or cycloalkyl group (preferably a $C_1$–$C_6$ alkyl or a $C_5$–$C_8$ cycloalkyl); each $R_2$ represents the same group selected from a hydrogen atom, an alkyl group, or a cycloalkyl group (preferably a $C_1$–$C_6$ alkyl or a $C_5$–$C_8$ cycloalkyl); and $R_3$ represents a hydrogen atom or an alkyl group (preferably $C_1$–$C_3$ alkyl group); $R_4$ represents the same groups as $R_1$; and each $R_5$ represents the same group selected from those equal to $R_2$.

The optically-active amino compounds subjected to racemization in this invention are those depicted by the above general formula. It is preferred that $R_1$, $R_4$ and $R_5$ in the formulas be an alkyl group having less than 6 carbon atoms, such as a methyl, ethyl, n- or iso-propyl, n-, iso-, or tert-butyl, pentyl, or heptyl group, or a cyclopentyl or cyclohexyl group. $R_2$ and $R_3$ may be the same or different, and it is preferable that they be a hydrogen atom, an alkyl group of less than 6 carbon atoms such as methyl, ethyl, n- or iso-propyl, n-, iso-, or tertbutyl, pentyl or heptyl group, a cyclopentyl or cyclohexyl group. Illustrative examples of the optically-active amine I above include, for instance, 2-amino-1-propanol, 2-amino-1-butanol, 2-amino-1-pentanol, 2-amino-1-hexanol, 2-amino-1-heptanol, 2-amino-1-octanol. N-methyl-2-amino-1-propanol, N-methyl-2-amino-1-pentanol, 2-amino-6-cyclopentyl-1-hexanol, 2-amino-5, 6-dimethyl-1-heptanol, 2-amino-4-ethyl-1-heptanol and the like. Illustrative examples of the optically active amine II above include, for instance, 1-amino-2-propanol, 1-amino-2-butanol, 2-amino-1-cyclopentyl ethanol, 1-amino-2-pentanol, 2-amino-1-(4-methylcyclohexyl) ethanol, 2-amino-1-(3-methylpentyl) ethanol, 2-amino-1-(4-methylcyclohexyl) ethanol, 1-amino-3-cyclohexyl-2-propanol and the like. Any optical purity of the above mentioned optically-active amino compounds is acceptable.

Thus, according to the present method one can obtain a racemic mixture of the amino alcohols I or II having substantially no optical activity from a mixture of optically-active amino alcohols which are initially rich in the enantiomer of lesser or no utility. The more valued enantiomer is separated by standard techniques known to those skilled in this art. For example, in the case of 2-amino-1-butanol, the levorotatory, l-2-amino-1-butanol is racemized according to the method of this invention to afford dl-2-amino-1-butanol. The latter is reacted with dextrorotatory tartaric acid to afford salts which are diastereoisomers of each other and, by crystal separation of said salts, dextrorotatory d-2-amino-1-butanol can be recovered. The d-2-amino-1-butanol is used as a starting material for manufacturing Ethambutol, a known pharmaceutical agent.

The present invention provides a simple method of racemizing an optically active amino alcohol to obtain greater amounts of the commercially useful enantiomer by using a combination of a specific catalyst and mild temperature and hydrogen pressure conditions. The process should preferably be carried out under dilute conditions where the amino alcohol is present in from 1 to 50 (preferably 5–30) weight percent based on the combined weight of amino alcohol and inert carrier. The present process can be conducted without the need for the use of corrosive and noxious reagent, such as ammonia, as required by the previously known processes.

The racemization occurs by contacting the optically active amino alcohol with granular Raney cobalt. The catalyst is formed from an initial alloy which contains from about 50 to 70 weight percent aluminum and from about 30 to 50 weight percent of cobalt. The alloy may further contain small amounts (from 0 to about 6 weight percent) of other metals such as chromium, molybdenum and the like.

The catalyst is prepared by contacting the starting alloy with an aqueous alkaline solution formed from an alkali or alkaline earth metal hydroxide, preferably sodium hydroxide. The alloy should be granular, that is have a particle size of from about 0.02 to 0.5 inch and preferably of from about 0.05 to 0.4 inch mean diameter. The activation is carried out in known manners by contacting the starting alloy with dilute, normally from about 1 to 10 wt. percent, preferably from 1 to 5 wt. percent, of an alkaline solution while maintaining a low temperature such as below about 50° C. and preferably below 40° C. Generally, it is best to activate the alloy at from about 20° C. to 40° C. Activation is readily monitored by the evolution of hydrogen and provides a suitable catalyst for use in the present process when from 20 to 40 percent of the aluminum is removed. The activated Raney cobalt catalyst is washed with water to free it from the alkaline solution and used immediately or stored under water or other inert atmosphere.

The process can be carried out in a pressure reactor of a batch-type or of a continuous type. The continuous type is preferably a trickle bed reactor having the above-described Raney cobalt a the packing therein. It is preferred that the optically-active amino alcohol starting material, an inert carrier solvent and the hydrogen gas be all permitted to flow concurrently through the trickle bed reactor. Various descriptions have been made about this mode of contact means including "Catalytic Reactor Design" by Tarhan (1983) and Hydrodynamics and Solid-Liquid Contacting Effectiveness in Trickle-Bed Reactors" by Gianetto et al. in AIChE Journal, Vol. 24, No. 6, page 1087.

The optically-active amino alcohols are introduced into the reactor as a solution. Any liquid for which the amino alcohol has solubility and which is inert can be used. The term "inert liquid" as used herein and in the appended claims means a material which is liquid under the reaction conditions and which is not substantially reactive with the amino alcohol or catalyst under the reaction conditions used. Examples of these include ethers, such as tetrahydrofuran, diethyl ether, methyl ethyl ether, glyme, diglyme and the like; aromatic hydrocarbons, such as toluene, benzene and the like as well as water.

The optically-active amino alcohol is contacted with the Raney cobalt catalyst in the presence of hydrogen. The hydrogen pressure within the reaction zone must be at an elevated pressure of from about 10 to 50 atmospheres, preferably from about 12 to 30 atmospheres. Where the reaction zone is a batch reactor, such as a pressure bomb-type reactor, the hydrogen gas is charged into the reactor in customary manners. When the reaction is run continuously, such as in a trickle bed reactor or the like, the hydrogen gas is introduced into the reaction zone at a rate sufficient to maintain a hydrogen pressure in the zone of from about 10 to 50 atmospheres, preferably from 12 to 30 atmospheres. The hydrogen pressure described above may be supplemented by partial pressure formed from an inert gas such as nitrogen.

The reaction zone should be maintained at an elevated temperature of from 100° C. to 175° C. and preferably from 120 to 175° C. The most preferred reaction temperature is from 120° C. to 160° C. Although higher temperatures may be used in certain cases, it normally provides a racemized product in lower yields.

The residence time of the optically-active amino alcohol in contact with the Raney cobalt catalyst under the conditions of the present processs should be sufficient to provide a high yield with high enantiomer equivalence as can be readily determined. It is realized that each amino alcohol will vary in the amount of time required to meet this criteria but normally will be from about 0.1 to 10 hours and normally from about 1 to 6 hours. The optimum time can be readily determined by simple experimentation by those skilled in this art.

It has been presently found that the racemization can readily occur to provide a product in high yield and with nearly 0% enantionmeric excess. The loss of material to by-product formation or by other means is minimal by the present process. Further the degree of racemization (as shown by optical rotation) is generally greater than attainable by other processes.

The following examples are given for illustrative purposes only and are not meant to be a limitation on the present invention except as defined by the claims appended hereto. All parts and percentages are by weight unless otherwise stated.

EXAMPLES

Granular Raney cobalt catalysts were prepared by treating granular alloys of aluminum and cobalt (60/40) of about 6 to 8 mesh (U.S. Standard Size) with dilute solutions of sodium hydroxide (about 5 wt. %) at a temperature of 35° C. ±2° C. while monitoring the hydrogen gas evolution. Hydrogen gas evolution was used to measure the degree and extent of activation of the alloy. Activation was continued until about 35% of the original aluminum in the alloy was removed (based on 1.5 moles of hydrogen per mole of aluminum.) The activated granules were washed with deionized water to a pH of 7.8 and then stored under water.

A series of racemization reactions were conducted in the following manner:

A 120 ml capacity magnetically stirred autoclave reactor was charged with 1 part of a ,50 percent aqueous slurry of the previously prepared Raney cobalt. The slurry was washed successively with isopropanol and then with diethyl ether to remove the water. 35.7 parts of dry diethyl ether and 1.89 parts R-(-)-2-amino-1-butanol (63% enantiomeric excess, e.e., by optical rotation) were added to the autoclave reactor. The reactor was pressurized to 250 psi with hydrogen gas and heated to a temperature which was maintained for a time indicated in the summary table below.

The reactor was cooled and depressurized. The contents were removed from the reactor, filtered and the solvent (diethyl ether) removed under vacuum to yield a clear liquid in very high yields (indicated below) and liquid which was very high in purity of 2-amino-1-butanol (by capillary gas chromatography using n-dodecane as internal standard). 400 MHz NMR and IR spectra were identical with that of the starting material in all cases confirming identity of the products. The products were analyzed by their optical rotation and by gas chromatography to determine enantiomeric excess. These results are shown in the table below. In all cases the resultant products were shown to have a high degree of conversion of the less desired enantiomer to the racemic mixture.

TABLE I

| Run | Press. (psi) | Temp. (°C.) | Time (hr.) | Recovered Product (%) | Purity (%) | e.e.* |
|---|---|---|---|---|---|---|
| 1 | 250 | 140 | 6.75 | 96 | 97 | 0 |
| 2 | 250 | 140 | 6.75 | 100 | 100 | 2 |
| 3 | 250 | 140 | 5.75 | 97 | 100 | 8 |
| 4 | 250 | 120 | 5.50 | 97 | | 0 |
| 5 | 250 | 120 | 4.75 | 100 | | 20 |

*by optical rotation; excess R-(−)

COMPARATIVE EXAMPLES

For comparative purposes, a process was carried out according to the process described in Japanese Published (Unexamined) Application Sho 51/6911 using the reaction conditions of Example I therein except that the catalyst was Raney cobalt as required by the instant invention.

A 120 ml autoclave reactor equipped with a magnetic stirrer was charged with the above described Raney cobalt. The slurry was washed as described above and dried to provide 1.5 grams of Raney cobalt. Also charged to the reactor was 14 ml of liquid ammonia and 5 grams of R-(-)-2-amino-1-butanol (69% e.e.). The reactor was charged with 50 atmospheres pressure of hydrogen gas and heated to 200° C. which was maintained for 5 hours.

Upon completion, the reactor was purged of gaseous material under vacuum. The reactor contents were removed and filtered. The product was analyzed in the manner described above. The yield of 2-amino-1-butanol was 76 percent. Distillation of the product gave a product with a specific rotation of -0.21° (2.1% e.e.).

The above experiment shows that the prior art method requiring the use of ammonia, provided lower yields of product and necessitated the use of special handling techniques to handle the required ammonia.

Again, for comparative purposes, the same process as described immediately above was repeated except that ammonia was not used and 9 grams of 2-amino-1-butanol (69% e.e.) was used. The yield was 41% 2-amino-1-butanol by gas chromatography. Distilled product showed specific rotation of -0.33° (3.3% e.e.). This example shows that when the process is carried out at high temperatures and without dilution of the amino alcohol the yield is substantially lowered.

What is claimed is:

1. A process of racemizing optically active mixtures of amino alcohols represented by either the formula:

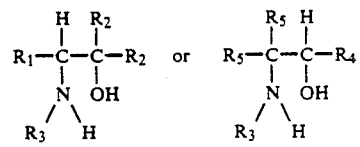

wherein $R_1$ and $R_4$ each independently represents an alkyl or cycloalkyl group; $R_2$ each represents a hydrogen atom; $R_3$ represents a hydrogen atom or an alkyl group, and $R_5$ represents the same group select from hydrogen, alkyl or cycloalkyl, said process consisting essentially of contacting in a reaction zone a solution consisting essentially of an inert liquid having from 1 to 50 weight percent of the amino alcohol mixture therein with Raney cobalt under a hydrogen pressure of from about 10 to 50 atmospheres and at a temperature of from 100° C. to 175° C. for a sufficient period of time to cause the racemization.

2. The process of claim 1 wherein the hydrogen pressure within the reaction zone is from 12 to 30 atmospheres and the solution contains from about 5 to 30 weight percent of amino alcohol.

3. The process of claim 1 wherein the temperature within the reaction zone is from 120° C. to 175° C.

4. The process of claim 2 wherein the temperature within the reaction zone is from 120° C. to 175° C.

5. The process of claim 1 wherein the reaction zone is a trickle bed reactor.

6. The process of claim 2 wherein the reaction zone is a trickle bed reactor.

7. The process of claim 3 wherein the reaction zone is a trickle bed reactor.

8. The process of claim 4 wherein the reaction zone is a trickle bed reactor.

9. The process of claim 1 wherein the amino alcohol has a general formula:

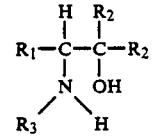

wherein, $R_1$ represents an alkyl or cycloalkyl group; $R_2$ each represent the same group selected from a hydrogen atom, and $R_3$ represents a hydrogen atom or an alkyl group.

10. The process of claim 4 wherein the amino alcohol has a general formula:

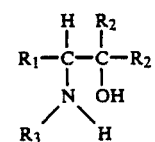

wherein, $R_1$ represents an alkyl or cycloalkyl group; $R_2$ each represent the same group selected from a hydrogen atom, and $R_3$ represents a hydrogen atom or an alkyl group.

11. The process of claim 5 wherein the amino alcohol has a general formula:

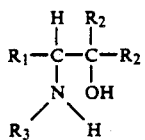

wherein, $R_1$ represents an alkyl or cycloalkyl group; $R_2$ each represent the same group selected from a hydrogen atom, and $R_3$ represents a hydrogen atom or an alkyl group.

12. The process of claim 8 wherein the amino alcohol has a general formula:

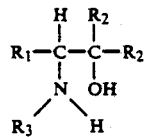

wherein, $R_1$ represents an alkyl or cycloalkyl group; $R_2$ each represent the same group selected from a hydrogen atom, and $R_3$ represents a hydrogen atom or an alkyl group.

13. The process of claim 1 wherein the amino alcohol has a general formula:

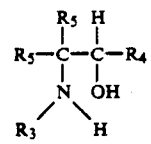

wherein, $R_5$ each represent the same group selected from hydrogen, an alkyl or cycloalkyl group; $R_4$ represents an alkyl or cycloalkyl group; and $R_3$ represents a hydrogen atom or an alkyl group.

14. The process of claim 4 wherein the amino alcohol has a general formula:

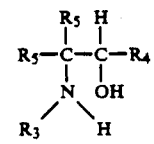

wherein, $R_5$ each represent the same group selected from hydrogen, an alkyl or cycloalkyl group; $R_4$ represents an alkyl or cycloalkyl group; and $R_3$ represents a hydrogen atom or an alkyl group.

15. The process of claim 5 wherein the amino alcohol has a general formula:

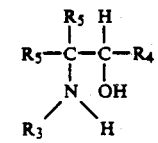

wherein, $R_5$ each represent the same group selected from hydrogen, an alkyl or cycloalkyl group; $R_4$ represents an alkyl or cycloalkyl group; and $R_3$ represents a hydrogen atom or an alkyl group.

16. The process of claim 8 wherein the amino alcohol has a general formula:

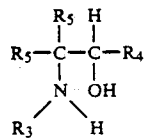

wherein, $R_5$ each represent the same group selected from hydrogen, an alkyl or cycloalkyl group; $R_4$ represents an alkyl or cycloalkyl group; and $R_3$ represents a hydrogen atom or an alkyl group.

17. The process of claim 9 wherein $R_1$ represents a group selected from a $C_1$-$C_6$ alkyl or a $C_5$-$C_8$ cycloalkyl group; each $R_2$ represents a group selected from a hydrogen atom group; and $R_3$ represents a group selected from a hydrogen atom or a $C_1$-$C_3$ alkyl group.

18. The process of claim 10 wherein $R_1$ represents a group selected from a $C_1$-$C_6$ alkyl or a $C_5$-$C_8$ cycloalkyl group; each $R_2$ represents a group selected from a hydrogen atom group; and $R_3$ represents a group selected from a hydrogen atom or a $C_1$-$C_3$ alkyl group.

19. The process of claim 11 wherein $R_1$ represents a group selected from a $C_1$-$C_6$ alkyl or a $C_5$-$C_8$ cycloalkyl group; each $R_2$ represents a group selected from a hydrogen atom group; and $R_3$ represents a group selected from a hydrogen atom or a $C_1$-$C_3$ alkyl group.

20. The process of claim 12 wherein $R_1$ represents a group selected from a $C_1$-$C_6$ alkyl or a $C_5$-$C_8$ cycloalkyl group; each $R_2$ represents a group selected from a hydrogen atom group; and $R_3$ represents a group selected from a hydrogen atom or a $C_1$-$C_3$ alkyl group.

21. The process of claim 13 wherein $R_3$ represents a group selected from hydrogen or a $C_1$-$C_3$ alkyl group; $R_4$ represents a group selected from a $C_1$-$C_6$ alkyl or a $C_5$-$C_8$ cycloalkyl group; and $R_5$ represents a group selected from a hydrogen atom, a $C_1$-$C_6$ alkyl or a $C_5$-$C_8$ cycloalkyl.

22. The process of claim 14 wherein $R_3$ represents a group selected from hydrogen or a $C_1$-$C_3$ alkyl group; $R_4$ represents a group selected from a $C_1$-$C_6$ alkyl or a $C_5$-$C_8$ cycloalkyl group; and $R_5$ represents a group selected from a hydrogen atom, a $C_1$-$C_6$ alkyl or a $C_5$-$C_8$ cycloalkyl.

23. The process of claim 15 wherein $R_3$ represents a group selected from hydrogen or a $C_1$-$C_3$ alkyl group; $R_4$ represents a group selected from a $C_1$-$C_6$ alkyl or a $C_5$-$C_8$ cycloalkyl group; and $R_5$ represents a group selected from a hydrogen atom, a $C_1$-$C_6$ alkyl or a $C_5$-$C_8$ cycloalkyl.

24. The process of claim 16 wherein $R_3$ represents a group selected from hydrogen or a $C_1$-$C_3$ alkyl group; $R_4$ represents a group selected from a $C_1$-$C_6$ alkyl or a $C_5$-$C_8$ cycloalkyl group; and $R_5$ represents a group selected from a hydrogen atom, a $C_1$-$C_6$ alkyl or a $C_5$-$C_8$ cycloalkyl.

25. The process of claim 17 wherein the amino alcohol is 2-amino-1-butanol.

26. The process of claim 18 wherein the amino alcohol is 2-amino-1-butanol.

27. The process of claim 19 wherein the amino alochol is 2-amino-1-butanol.

28. The process of claim 20 wherein the amino alochol is 2-amino-1-butanol.

* * * * *